United States Patent [19]

Fregly et al.

[11] Patent Number: 5,147,650
[45] Date of Patent: Sep. 15, 1992

[54] COMPOSITIONS AND METHODS FOR ACHIEVING IMPROVED PHYSIOLOGICAL RESPONSE TO EXERCISE

[75] Inventors: Melvin J. Fregly; R. Malcolm Privette; Robert Cade, all of Gainesville, Fla.

[73] Assignee: University of Florida, Gainesville, Fla.

[21] Appl. No.: 636,329

[22] Filed: Dec. 31, 1990

Related U.S. Application Data

[63] Continuation-in-part of Ser. No. 378,582, Jul. 17, 1989, Pat. No. 4,981,687, which is a continuation-in-part of Ser. No. 226,027, Jul. 29, 1988, abandoned.

[51] Int. Cl.$^5$ .................... A61K 47/00; A61K 33/14; A61K 31/70; A61K 31/52
[52] U.S. Cl. .................... 424/439; 424/679; 514/23; 514/264; 514/557; 514/738; 514/832
[58] Field of Search .............. 514/23, 557, 738, 832, 514/264; 424/439, 679

[56] References Cited

U.S. PATENT DOCUMENTS

| | | | |
|---|---|---|---|
| 4,042,684 | 8/1977 | Kahm | 514/23 |
| 4,322,407 | 3/1982 | Ko | 514/23 |
| 4,839,347 | 6/1989 | Franz | 514/23 |
| 4,874,790 | 9/1989 | Stanko | 514/557 |
| 4,981,687 | 1/1991 | Fregley et al. | 514/557 |
| 5,028,446 | 7/1991 | Saleeb et al. | 562/595 |

FOREIGN PATENT DOCUMENTS 1948111  4/1970  Fed. Rep. of Germany ...... 514/738

OTHER PUBLICATIONS

Ferguson, M., M. M. O'Brien (1960) "Heat Stroke in New York City: Experience with Twenty-Five Cases," NY State J. Med. 60:2531-2538.

Costill, D. L., K. E. Sparks (1973) "Rapid fluid replacement following thermal dehydration," J. Appl. Physiol. 34(3):299-303.

Greenleaf, J. E. (1979) "Hyperthermia and Exercise," In *International Review of Physiology: Environmental Physiology III*, vol. 20, D. Robertshaw, ed., University Park Press, Baltimore, pp. 157-208.

Felig, P., A. Cherif, A. Minagawa, J. Wahren (1982) "Hypoglycemia during prolonged exercise in normal men," N. Engl. J. Med. 306(15):895-900.

Riedesel, M. L., D. Y. Allen, G. T. Peake, K. Al-Qattan (1987) "Hyperhydration with glycerol solutions," J. Appl. Physiol. 63(6):2262-2268.

Lyons, T. P., M. L. Riedesel, L. E. Meuli (1987) "Physiological costs of exercise following hyperhydration with glycerol," Temperature Regulation I (35-40), p. 323 (abstract).

Allen, D. Y., M. L. Riedesel (1985) "Overhydration following ingestion of glycerol solution," Environ. Physiol. II (3713-3720), p. 1046 (abstract).

Riedesel, M. L. (1987) "Oral Glycerol Solutions as a Deterrent to Dehydration During Heat Exposure," *Department of the Air Force Report*, AD-A118746.

Meuli, L. E., T. Lyons, M. L. Riedesel (1988) "Plasma ADH and aldosterone levels following glycerol induced hyperhydration," Exercise II (1309-1314) p. a521 (abstract).

(List continued on next page.)

Primary Examiner—Robert T. Bond
Assistant Examiner—E. C. Ward
Attorney, Agent, or Firm—Saliwanchik & Saliwanchik

[57] ABSTRACT

Disclosed here are novel compositions and methods which can be used to reduce or prevent adverse physiological effects of physical exercise or environmental exposure. The novel compositions comprise fluids containing water, sugar, electrolytes, and a substance which is non-toxic to man or animals, can be rapidly absorbed through the gastrointestinal tract, prevents decreases in blood volume, and acts as an energy source.

5 Claims, 7 Drawing Sheets

OTHER PUBLICATIONS

Maughan, R. J., M. Gleeson (1988) "Influence of a 36 h fast followed by refeeding with glucose, glycerol or placebo on metabolism and performance during prolonged exercise in man," Eur. J. Appl. Physiol. 57:570–576.

Gleeson, M., R. J. Maughan, P. L. Greenhaff (1986) "Comparison of the effects of pre-exercise feeding of glucose, glycerol and placebo on endurance and fuel homeostasis in man," Eur. J. Appl. Physiol. 55:645–653.

Terblanche, S. E., R. D. Fell, A. C. Juhlin-Dannfelt, B. W. Craig, J. O. Holloszy (1981) "Effects of glycerol feeding before and after exhausing exercise in rats," J. Appl. Physiol. 50(1):94–101.

Miller, J. M., E. F. Coyle, W. M. Sherman, J. M. Hagberg, D. L. Costill, W. J. Fink, S. E. Terblanche, J. O. Holloszy (1983) "Effect of glycerol feeding on endurance and metabolism during prolonged exercise in man," Medicine and Science in Sports and Exercise 15(3):237–242.

TIME TO REACH RECTAL TEMP. OF 38 DEG.

COMPOSITIONS AND METHODS FOR ACHIEVING IMPROVED PHYSIOLOGICAL RESPONSE TO EXERCISE

CROSS-REFERENCE TO A RELATED APPLICATION

This application is a continuation-in-part of our copending application Ser. No. 07/378,582, filed Jul. 17, 1989, now U.S. Pat. No. 4,981,687, which is a continuation-in-part of our copending application Ser. No. 07/226,027, filed Jul. 29, 1988, now abandoned.

BACKGROUND OF THE INVENTION

In humans and other animals, strenuous exercise as well as exposure to sunlight and heat can result in significant physiological changes. Subjects exercising or working in the heat are at risk for developing heat related injuries. Environmental heat illnesses include heat syncope, heat exhaustion, dehydration syndrome, and heat stroke. The potentially fatal clinical syndrome of heat stroke has been described in marathon runners, military recruits, football players, and in hot industrial environments. An epidemic appearance of heat stroke has been described during heat waves in urban areas (Ferguson, M., and M. M. O'Brien [1960] "Heat Stroke in New York City: Experience with 25 Cases," N.Y. State J. Med. 60:2531-2538).

The "dehydration syndrome" is characterized by loss of appetite and limited capacity for work. Evidence of heat exhaustion becomes apparent with losses of 5% of the body water, and at 7% disorientation and hallucinations occur. Losses of body water of 10% or greater are extremely hazardous and lead to heat stroke and death if not treated immediately. Heat stroke is accompanied by high body temperature (106°-110° F.), deep coma, and in most cases there is complete absence of sweating, and failure of the major organ systems.

Three factors determine the thermal balance of the body: metabolic heat production, heat exchange between the organism and its surroundings, and heat loss by the evaporation of sweat (Knochel, J. P. [1980] "Clinical physiology of heat exposure," In *Clinical Disorders of Fluid and Electrolyte Metabolism*, M. H. Maxwell and C. R. Kleeman, eds., McGraw-Hill, New York). For the subject exercising or working, particularly in a hot environment, the capacity to dissipate metabolically produced heat depends for the most part on the subject's ability to form and vaporize sweat (Costill, D. L. and K. E. Sparks [1973] "Rapid fluid replacement following thermal dehydration," J. Appl. Physiol. 34(3):299-303; Greenleaf, J. E. [1979] "Hyperthermia and exercise," Int. Rev. Physiol. 20:157-208).

During exercise in a hot environment, serious deficits in effective circulating volume may occur. Muscular work, independent of environment, results in massive shunting of blood to skeletal muscle, along with a substantial loss of plasma volume into the working muscle. Moreover, effective circulating volume is also diminished by losses of sweat (Knochel [1980] supra). The deficit in intravascular volume impedes the delivery of heated blood to the periphery for evaporative cooling. Thus, in the dehydrated exercising subject, there is a progressive increase in the core body temperature as sweat losses accumulate. Indeed, salt and water depletion are important predisposing factors to the development of heat-related illnesses.

Exercise is characterized by a marked increase in glucose utilization. The exercising muscle has a greatly increased need for energy. Some of the glucose needed for energy comes from liver glycogen stores. With prolonged exercise, liver glycogen stores are depleted and the rate of glucose production fails to keep pace with glucose utilization, resulting in a fall in the blood glucose concentration. The development of frank hypoglycemia has been described in marathon runners (Felig, P., A. Cherif, A. Minagawa et al. [1982] "Hypoglycemia during prolonged exercise in normal men," N. Engl. J. Med. 306(15):895-900).

Notable among the many physiological responses to physical exertion are increased body temperature, perspiration and pulse rate, a decrease in the blood volume, and biochemical changes associated with the metabolism of compounds to produce energy.

One metabolic change which is associated with continued physical exertion is a shifting of the type of compound used as the primary energy source. In the absence of physical exertion, the metabolism of fat is a primary energy source for the body. During times of exertion, carbohydrates are increasingly used as a source of readily available energy. The body continues to utilize carbohydrates as a major source of energy during prolonged periods of exercise.

If, however, the exercise is particularly strenuous or long in duration, the supply of readily available carbohydrates may become depleted and the body is forced to utilize another source of energy. The metabolism of proteins fills the energy void caused by the depletion of carbohydrates. Unfortunately, the metabolism of protein is not an efficient source of energy for the exercising individual. Protein metabolism results in the utilization of amino acids. This amino acid utilization can result in the depletion of essential amino acids in the plasma. The loss of amino acids can detrimentally affect the person or animal in many ways. One detrimental effect of the depletion of amino acids is a reduction on the body's ability to repair tissue which is damaged in the course of the strenuous exercise.

Attempts have been made to counteract the adverse effects of strenuous exertion. For example, the consumption of water helps to maintain body temperature and blood volume. This technique has met with very limited success, however. Also, products have been developed recently which combine sugar and electrolytes with water. One well known example of this type of product is GATORADE® which contains 21 milliequivalents per liter (21 meq/l) of sodium, 2 meq/l potassium, and 6% sucrose. The GATORADE® composition is described in British Patent No. 1,252,781, which issued to Bradley et al. Other such compositions are known and are described, for example, in U.S. Pat. Nos. 4,042,684 and 4,322,407.

It is well known that glycerol (glycerin) can be ingested safely. Limited clinical studies have suggested that glycerol, in solution with water, may be used to induce hyperhydration (Riedesel, M. L., D. Y. Allen, G. T. Peake, and K. Al-Quattan [1987] "Hyperhydration with glycerol solutions," J. Appl. Physiol. 63(6):2262-2268). The work of the Riedesel group which was described in the 1987 publication has also been described, in part, in other places. In a 1985 abstract and in a 1987 abstract, Riedesel and coworkers reported that ingestion of an approximately 23% glycerol solution in saline resulted in overhydration of the subjects. The two abstracts had conflicting results regarding whether sweat rates were increased (Lyons et al. [1987] "Physiological Costs of Exercise Following Hyperhydration with Glycerol," Temperature Regulation I (35-40), p. 323 [abstract]; Allen et al. [1985] Environ. Physiol. II [3713-3720] p. 1046 [abstract]). In a 1987 report to the Air Force, Riedesel reported overhydration of rats which were fed glycerol (Riedesel [1987] "Oral Glycerol Solutions as a Deterrent to Dehydration During Heat Exposure," Department of the Air Force Report, AD-A118746). In a 1988 abstract Riedesel et al. again reported hyperhydration and decreased urine output after glycerol ingestion (Meuli et al. [1988] Exercise II [1309-1314] p. a521).

Other researchers have also examined the effects of glycerol ingestion. Maughan and Gleeson found that ingestion of large amounts of glycerol after a 36 hour fast did not significantly improve performance of exercising subjects (Maughan et al. [1988] The Eur. J. Appl. Physiol. 57:570-576). In fact, for one of the control groups, exercise duration after glycerol ingestion was lower than after water ingestion alone. This 1988 article confirms earlier work by Gleeson and Maughan which found that ingestion of large amounts of glycerol did not enhance exercise performance (Gleeson et al. [1986] The Eur. J. Appl. Physiol. 55:645-653).

Researchers at Washington University School of Medicine have also examined the effects of glycerol ingestion. In 1981 the Washington University group reported that glycerol-fed rats had increased endurance, apparently because glycerol protected against hypoglycemia (Terblanche et al. [1981] J. Appl. Physiol 50(1):94-101). Significantly, however, two years later the Washington group found that glycerol did not increase endurance in man when administered according to their protocol (Miller et al. [1983] Medicine and Science in Sports and Exercise 15(3):237-242). These published reports on the effects of glycerol have revealed that ingestion of large amounts of glycerol can result in decreased urine output and hyperhydration. Several studies have specifically looked at the effect of glycerol on endurance, and each of these studies has found that glycerol in large doses does not appear to increase endurance in man.

Much of the previous research has focused on the ability of glycerol to cause water retention. However, water retention alone has little or no correlation with enhanced endurance or physiological performance. In order to have a beneficial effect on endurance and performance, the water must be appropriately allocated throughout the body. It is not enough to simply reduce urine output. Water must be available for sweating, cells cannot be dehydrated, and plasma volume must be maintained. Only if these physiological objectives are met can endurance and performance be enhanced. This enhancement of the physiological response to exercise and heat can be largely attributed to efficient cooling of the body.

Osmotic pressure is primarily responsible for the direction and rate of movement of water across membranes in the body. The general concepts of osmosis and osmotic pressure are very well known chemical phenomena whereby water moves across a semipermeable membrane in such a way as to make its thermodynamic activity uniform across the entire system. Thus, water will move across a semipermeable membrane such that the net flow of water will be across the membrane into the fluid which initially had the highest concentration of solutes. The allocation of water between digestive organs, blood plasma, and cells depends upon the relative osmotic pressures between these sites. Although it has been established that the ingestion of massive amounts of glycerol results in the retention of water within the body, i.e., the rate of urine flow is decreased, this observation alone produces no information as to whether the body's physiological responses to heat or physical exertion have been enhanced. For example, a large concentration of glycerol in the stomach or intestine can cause water to move across the gastrointestinal membranes into the digestive tract. This might cause detrimental responses to physical exertion and heat exposure. Also, high concentrations of glycerol in the blood plasma can cause water to leave the cells and enter the plasma. Again, the resulting dehydration of the cells could have detrimental effects on the person or animal.

Studies where large amounts of glycerol have been administered in short time periods have not shown beneficial physiological effects. The researchers have observed water retention, but none have demonstrated any effect which would enhance endurance or lessen a person's discomfort. These studies do not establish any relationship between the administration of glycerol and actual physiological responses to exercise or heat exposure. Also, no studies have examined the physiological effects of glycerol or related compounds in solution with compounds other than water or saline.

Thus, the focus of glycerol research in the past has been primarily to achieve random generalized water retention. By contrast, the research which has led to the subject invention concentrated on achieving appropriate water distribution within the body. This has led to the formulation of a novel composition which greatly enhances the physiological response to physical exertion and heat exposure.

Although GATORADE® does help to combat some of the negative effects resulting from physical exertion, long distance runners and other athletes who must endure long periods of strenuous exercise still suffer the effects of decreased blood volume and a loss of energy-providing carbohydrates.

The invention described here is a novel fluid composition which surprisingly and advantageously maintains blood volume at levels well above those observed in the absence of fluids or even with GATORADE®. The novel product has the additional advantage of providing an energy source. Further, users of the product report lower levels of perceived difficulty of exercise when the novel fluid composition is used.

BRIEF SUMMARY OF THE INVENTION

The subject invention relates to novel compositions and methods for ameliorating the adverse physiological effects which can result from physical exertion and heat exposure. The subject invention can be used with humans and other animals. Described here is a novel fluid composition comprising
(a) water;
(b) electrolytic compound(s);
(c) sugar; and
(d) an additional compound which is characterized by:
  (i) non-toxic to man or animals;
  (ii) is rapidly absorbed through the gastrointestinal tract;
  (iii) prevents the decrease of blood volume; and
  (iv) is an energy source wherein the concentration of said additional compound(s) is from about 0.5% to about 10%. More preferably, the concentration of said additional compound may be from about 0.5% to about 5%.

One example of said additional compound is glycerol. Other compounds which may be used according to the subject invention include pyruvate and/or lactate, which are particularly useful because they function to enhance the energy available for working muscles. The presence of pyruvate or lactate improves performance and helps to prevent the detrimental breaking down of protein as an energy source. The compounds added to the electrolyte/glucose solution may be used in the solution individually or in combination.

Also described here are unique methods, involving the use of the novel fluid composition, for ameliorating the adverse effects which can result from physical exertion, heat exposure, exposure to cold, and blood loss.

BRIEF DESCRIPTION OF THE DRAWINGS

The invention can be better understood with reference to the following drawings in which.

DETAILED DESCRIPTION OF THE INVENTION

The invention described here is a novel composition which has been shown to improve the physiological response in animals, including humans, to physical exercise and environmental exposure. Specifically, the invention comprises a fluid which contains, as one of the ingredients, glycerol or an ester of glycerol, or any other analog or derivative of glycerol which is non-toxic to animals, can be rapidly absorbed through the gastrointestinal tract, distributed into plasma and extracellular fluid, but is not transferred, or is transferred poorly, into the brain. As used hereinafter, the term glycerol refers to glycerol itself and any ester, analog, or derivative which has the same function as glycerol in the composition described here. Instead of glycerol, or in addition to glycerol, the composition may contain pyruvate. Other compounds satisfying the aforementioned characteristics can be found in standard medical or pharmacology reference books.

The novel fluid's surprising and beneficial physiological effects on the body during exercise or environmental exposure include maintenance of blood volume and cardiac output, readily available energy source, improved skin blood flow, prevention or delay of onset of hyperthermia, increased rate of movement of electrolytes across the gastrointestinal wall, reduction in the breakdown of proteins and associated metabolism of essential amino acids, and decreased time needed for repair of body tissue following strenuous exercise.

When the fluid of the subject invention is administered, the body's physiological response to exercise or environmental exposure is greatly enhanced compared to the response when the body receives no fluids, receives only water, or receives fluids such as GATORADE ® which contain electrolytes and a sugar source in addition to water. Thus, the novel composition described here can be used to ameliorate the adverse effects of physical exertion or environmental exposure. As used herein, the term "ameliorating the adverse effects of physical exertion or environmental exposure" refers to the achievement of one or more of the following: prevention of plasma volume decrease, increased respiratory quotient, reduced rate of increase of rectal temperature, reduced pulse rate, or increased cardiac output; combined with either enhanced endurance or performance, lower perceived difficulty of a physical task, or an enhanced ability to withstand heat exposure or chronic exposure to cold. The many advantages of the novel fluid composition (designated $TQ_2$) described here are clearly shown in FIGS. 1 through 7. The $TQ_2$ which was administered to exercising individuals in order to achieve the results discussed below was primarily water. In addition to the water, the composition comprised glucose (4%), potassium (2 meq/l), sodium (26 meq/l), phosphate (4 meq/l), and glycerol (3%).

Figure 1:
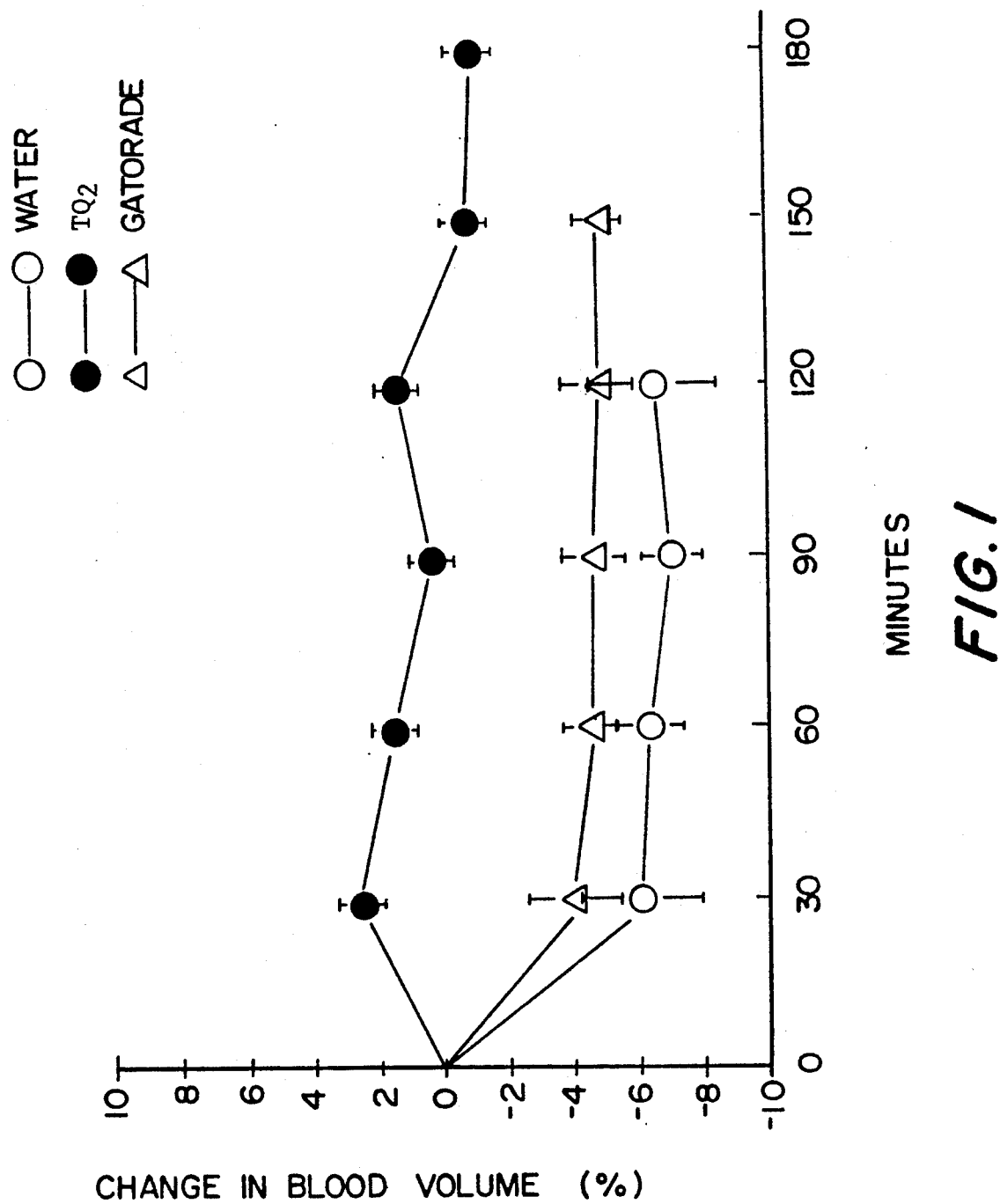
FIG. 1 shows the changes in blood volume of three trials of human subjects working at 75-80% of their maximal rate of oxygen on a bicycle ergometer. The trials are designated in the figure. One standard error is set off at each mean. This figure shows that only the group which was given $TQ_2$ (15 minutes before initiation of exercise [200 ml], at 15 min, 45 min, and every half hour thereafter) was able to maintain their blood volume during the period of exercise.
Figure 2:
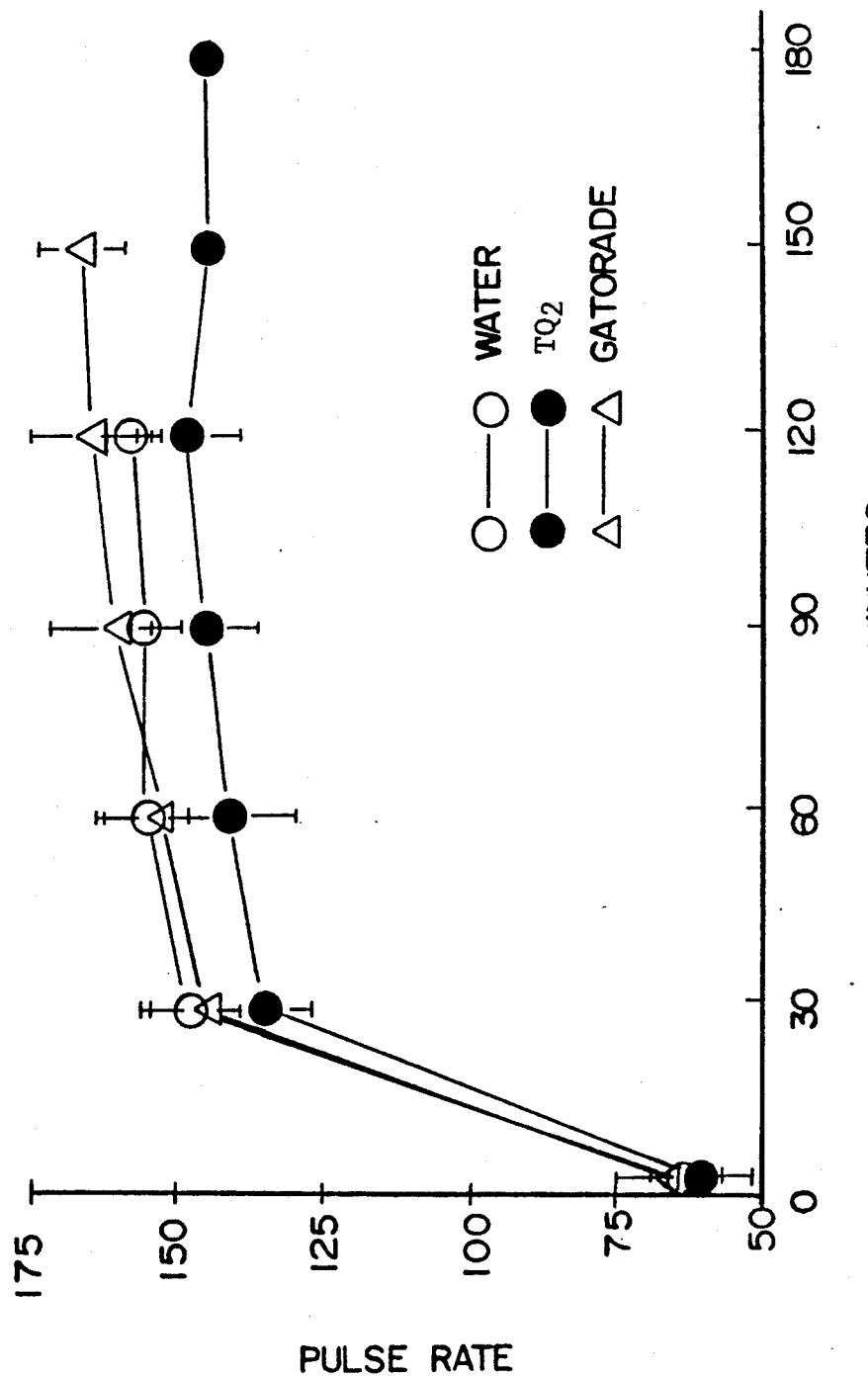
FIG. 2 shows that the pulse rate of the group receiving $TQ_2$ was maintained at a lower value than the other two trials during the course of exercise. The trials are the same as those shown in FIG. 1. One standard error is set off at each mean.

One important advantage of $TQ_2$ is that it allows the body to maintain the volume of blood at levels close to the pre-exercise volume. Even where water or GATORADE ® are given to the exercising person, significant decreases in blood volume are observed. The blood volume comparisons are shown in FIG. 1. FIG. 2 illustrates the ability of the novel fluid composition to prevent the elevation of heart rate to the level of that observed for subjects receiving either water or GATORADE ®.

Figure 3:
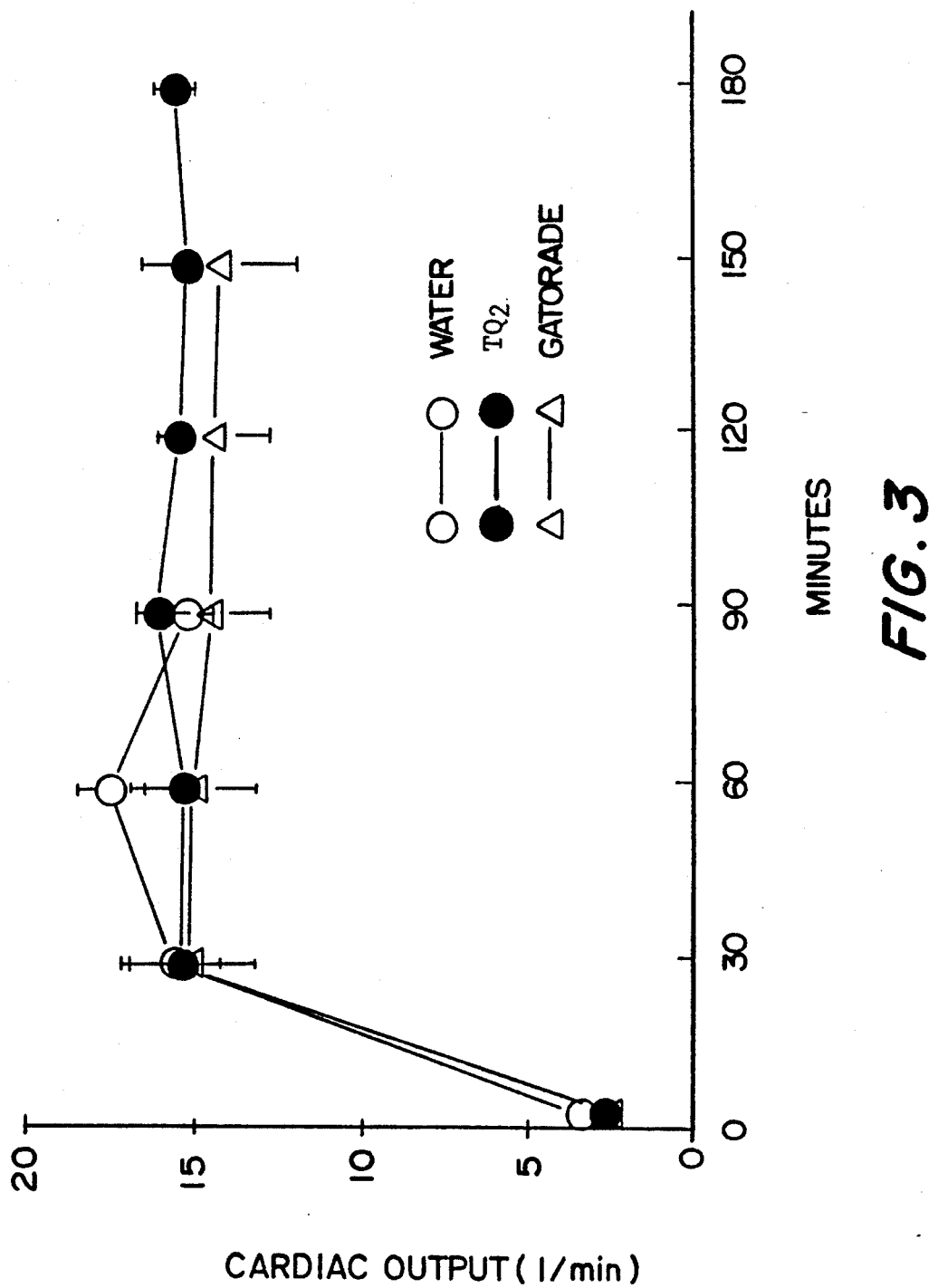
FIG. 3 shows the high level of cardiac output achieved in connection with the administration of $TQ_2$.
Figure 4:
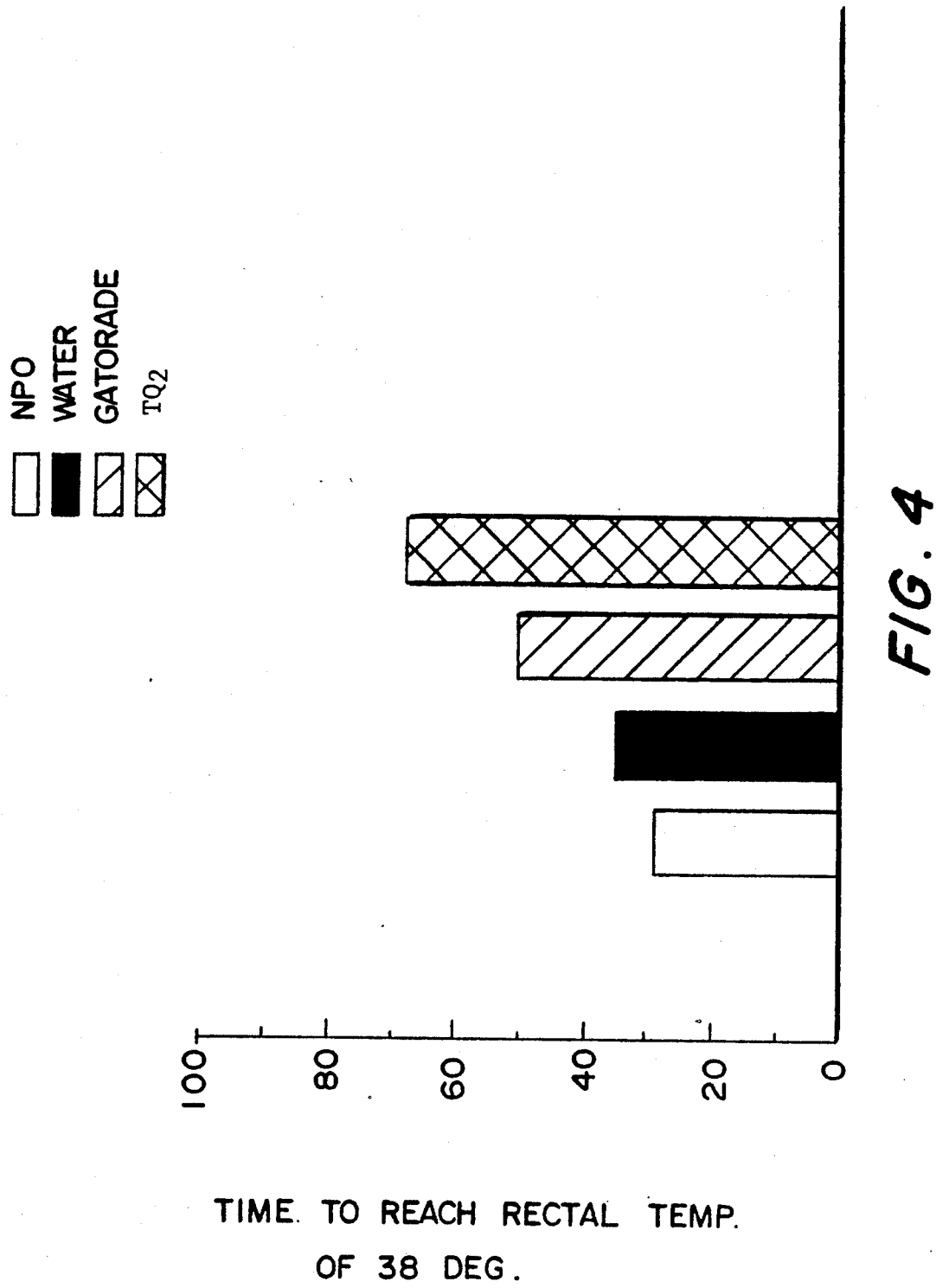
FIG. 4 shows the time required to reach a rectal temperature of 38° C. by the three trials shown in FIG. 1, as well as an additional group receiving nothing per os (NPO) prior to the exercise.
Figure 5:
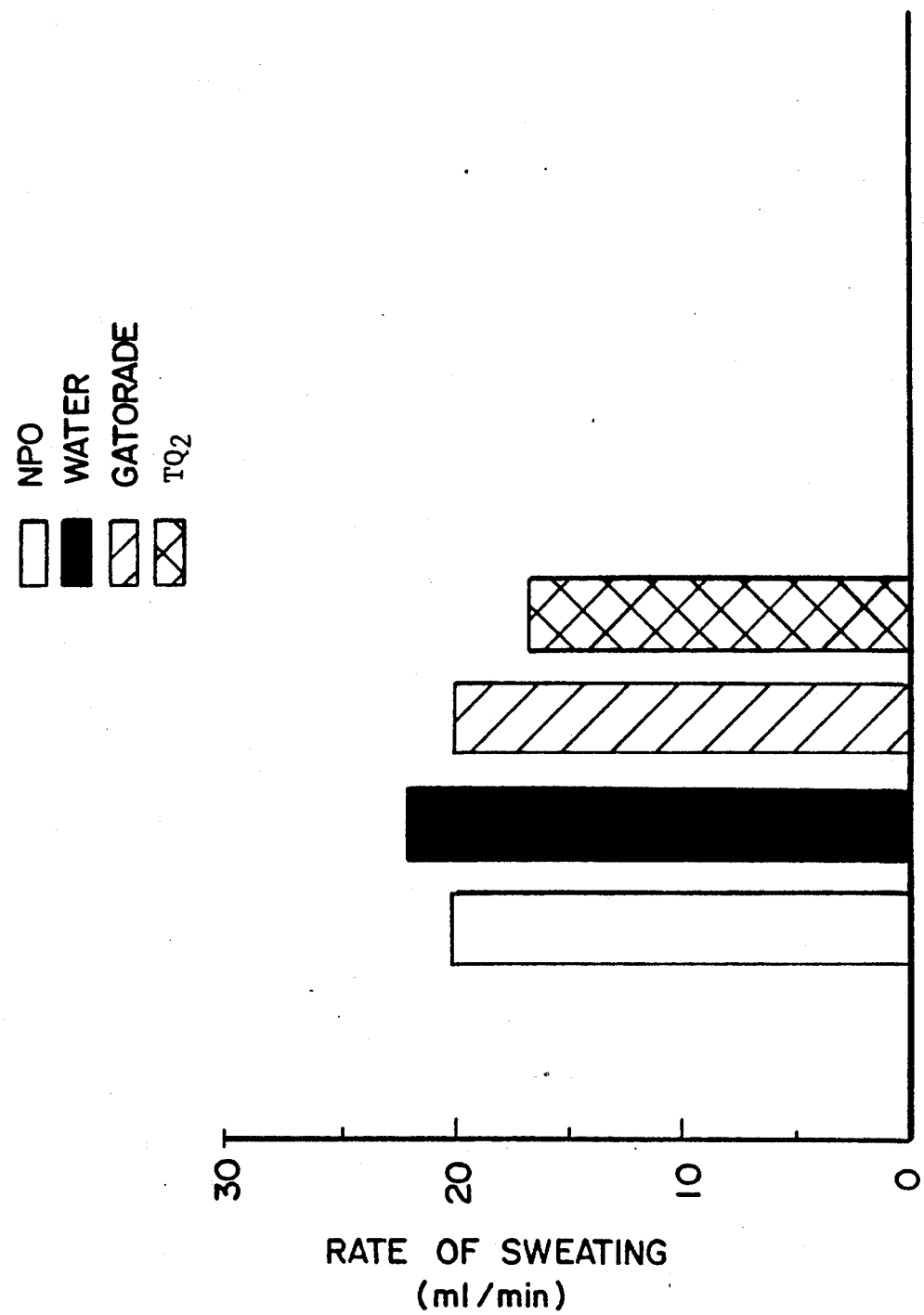
FIG. 5 shows the mean rates of sweating of the same four trials as in FIG. 3.
Figure 6:
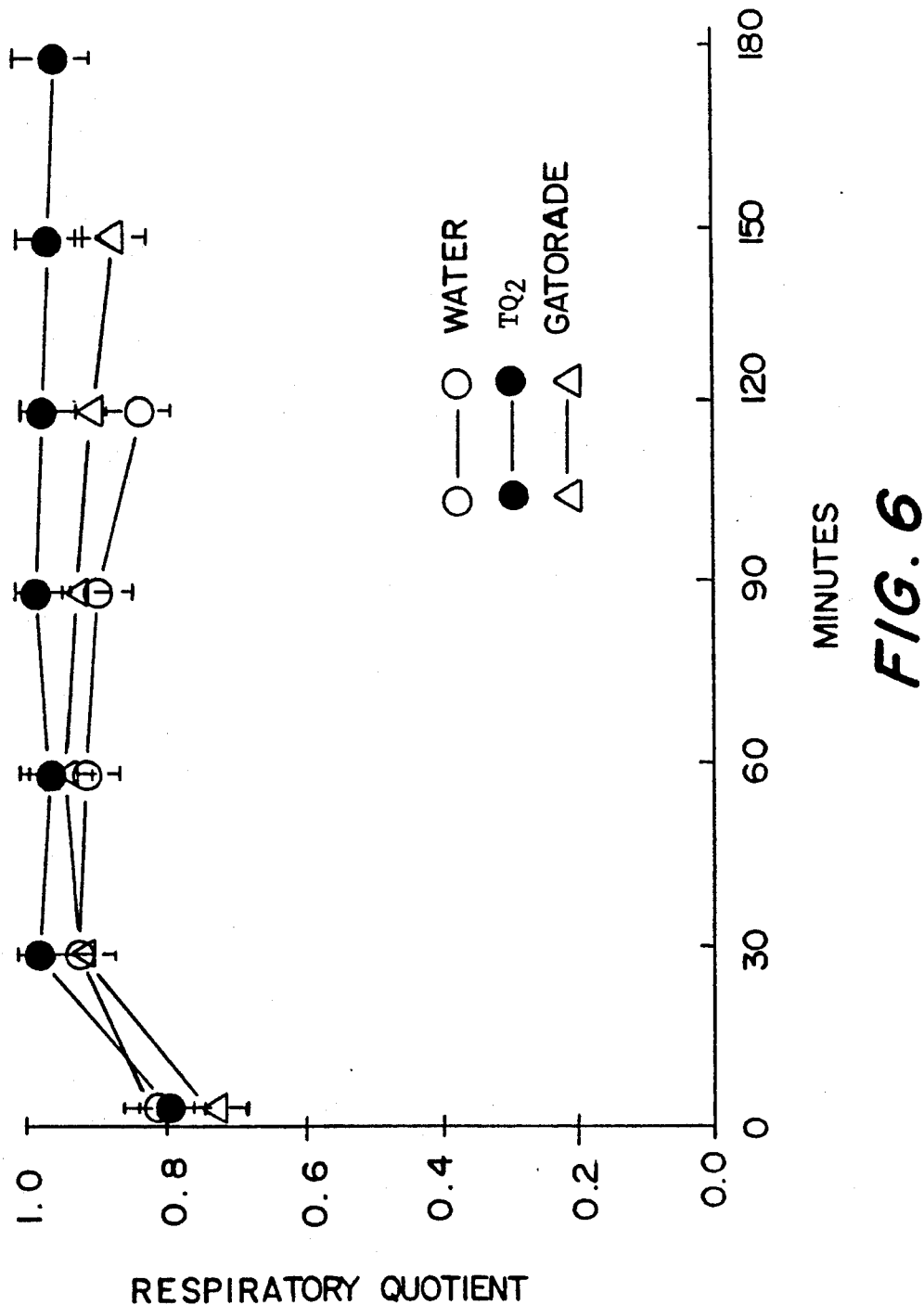
FIG. 6 shows the respiratory quotient ($[CO_2]/[O_2]$) as a function of exercise time. Respiratory quotient is an indication of the metabolic energy source being utilized.

When the novel fluid composition is administered, cardiac output is advantageously sustained at a high level, even over extended periods of exertion. FIG. 3 illustrates this effect. Increases in body temperature during exercise occur much more slowly when the novel fluid composition is given than when no fluids are administered or when either water or traditional GATORADE ® are administered. FIG. 4 shows that, on the average, it takes more than 30% longer for rectal temperature to reach 38° C. when $TQ_2$ is used than when GATORADE ® is used. It is possible to exercise for well over 1 hour at 75-80% of maximal rate of oxygen consumption without reaching a body temperature of 38° C. when $TQ_2$ is administered. Also, a marked decrease in the rate of sweating is observed for individuals given the novel fluid composition of the subject invention. This decrease in sweat rate is shown in FIG. 5. The decrease in sweat rate is significant because this suggests that the body is being cooled more efficiently.

This can be attributed to increased blood volume which results in improved peripheral circulation and movement of blood near the skin surface. This surface circulation is very important in the effective dissipation of body heat.

Further evidence suggests that the use of $TQ_2$ results in an increase in the proportion of energy derived from carbohydrates as opposed to energy derived from the metabolism of fat or protein. This unexpected and advantageous result can be seen from FIG. 6 which shows the respiratory quotient as a function of time. Respiratory quotient, which is defined as the ratio of carbon dioxide output to oxygen input, is an indication of the type of compounds which are being metabolized as an energy source for the exercising person or animal. For metabolism of carbohydrates, the respiratory quotient is 1.0. The respiratory quotient for metabolism of fats or proteins is less than 1.0. If fat is the primary source of energy, then the respiratory quotient is approximately 0.6. A respiratory quotient of approximately 0.8 can be expected if the cells are burning half fat and half carbohydrates. Thus, the higher respiratory quotients shown in FIG. 6 for $TQ_2$ indicate that these individuals are utilizing a greater proportion of carbohydrates as their energy source. The increased use of carbohydrates can have important physiological advantages, especially when strenuous exercise is maintained over a long period of time. For example, carbohydrate metabolism is preferable to fat metabolism because it is a quicker and more efficient source of immediate energy. Further, carbohydrates are preferred as an energy source over proteins because protein metabolism can cause the depletion of essential amino acids. The depletion of amino acids can have adverse physiological effects including a reduction in the body's ability to repair muscle which is damaged in the course of exercise.

To further enhance the energy sources available to cells, pyruvate may be added to the novel composition. It has also been found that by administering pyruvate, it is possible to maintain a relatively steady concentration of pyruvate for use by cells as an energy source. Addition of a small amount of pyruvate, given at frequent intervals, improves performance and endurance, apparently because it enhances entrance of acetyl CoA into the Krebs cycle. The Krebs cycle is a well known, but very complicated, biochemical pathway which provides a working muscle with its energy source. A detailed description of the Krebs cycle can be found in most biochemistry textbooks, including Lehninger (Lehninger, A. J. *Biochemistry: The Molecular Basis of Cell Structure and Function*, 2ed., Worth Publishers, Inc.: New York, pp. 444–449, 1975).

Pyruvate normally is formed from glucose but, during vigorous exercise, pyruvate may not be formed fast enough to keep up with cellular demand. Thus, the concentration of pyruvate drops markedly. This loss of available pyruvate not only deprives cells of their primary carbohydrate energy source, but also inhibits the metabolism of fats as an energy source. Fats enter the Krebs cycle as acetyl CoA. Acetyl CoA, which is formed as a result of the breakdown of long chain fatty acids, apparently does not enter in the Krebs cycle properly if pyruvate is not present. When acetyl CoA is not metabolized in the Krebs cycle, it is converted to acetoacetic acid, which does not act as a ready energy source. Therefore, when pyruvate is available in short supply, the cells are deprived of their primary carbohydrate source, and they cannot effectively metabolize fats either. Thus, the cells can be forced to depend upon amino acid metabolism in order to derive energy. If the concentration of pyruvate falls during vigorous exercise, no fuel can enter the Krebs cycle, and the cell, in effect, starves. By administering the novel composition described here, blood pyruvate is stabilized at a level sufficient to assure adequate energy supplies. Lactate may be used instead of, or in addition to, pyruvate in the current invention.

Figure 7:
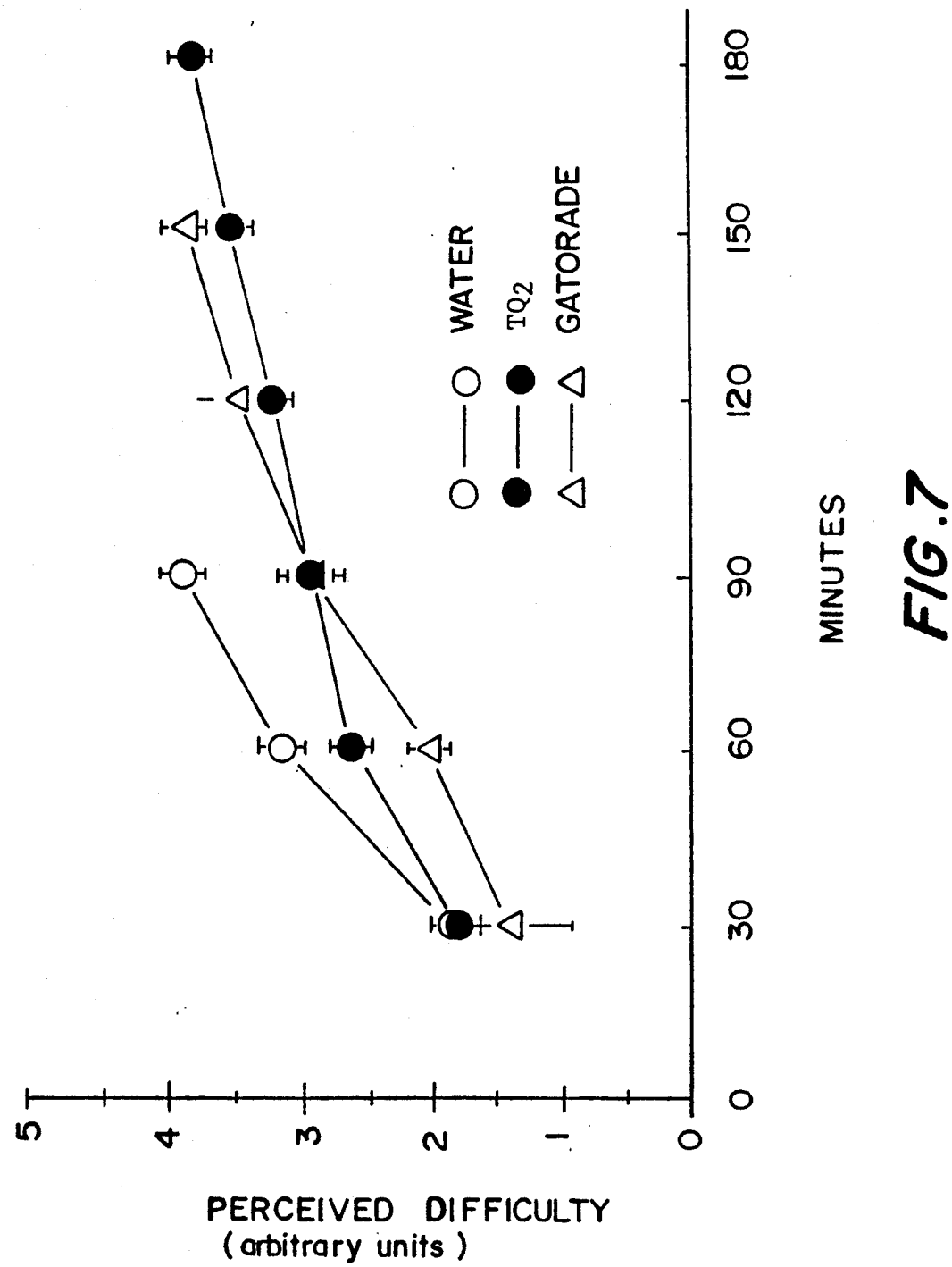
FIG. 7 shows the perceived difficulty (in arbitrary rating units) of the exercise as scored by observers during the exercise.

An additional important indicator of the novel fluid composition's effectiveness is illustrated in FIG. 7. This figure shows a significant lowering of the perceived difficulty of long term exercise among individuals to whom $TQ_2$ is administered. Although all individuals naturally perceive an increase in difficulty of exercise as the exercise is maintained for long periods of time, individuals who were given $TQ_2$ showed a significantly reduced rate of increase in the perceived difficulty of the exercise. The trial ingesting water showed the normal perceived difficulty within 90 minutes of beginning exercise while in the trail receiving GATORADE® reached the same level of perceived difficulty after 150 minutes of exercise. The trial receiving $TQ_2$ reached this level after 180 minutes. The lower difficulty perceived by individuals receiving $TQ_2$ could lead to enhanced physical performance, especially when long term exercise, such as marathons, are involved.

The novel fluid composition of the subject invention can be used to improve the physiologic response of any animal undergoing exercise or being subjected to high temperature conditions. For example, humans, horses, dogs, mules, oxen, camels, elephants, sheep, cows, and pigs are a few of the animals which can benefit from the administration of the novel fluid composition described here. The fluid of the subject invention can also be used to alleviate or prevent dehydration which is known to result from chronic exposure to cold temperatures.

The fluid of the subject invention can be administered to an animal orally, intravenously, or by any other means of conveying said fluid into the tissues of the animal.

Following are examples which illustrate materials, methods and procedures, including the best mode, for practicing the invention. These examples are illustrative and should not be construed as limiting. Where concentrations are expressed as percentages, these percentages refer to weight ratios.

EXAMPLE 1

For use in humans or other animals which are about to undergo, are undergoing, or have recently undergone physical exercise, a novel fluid composition comprising water, a sugar source, electrolytes, and glycerol can be administered orally.

The composition, which is predominantly water, may contain between about 0.5% to about 5% glycerol. Preferably, the composition may contain about 1% to about 1.5% glycerol. The sugar of the composition may be sucrose, glucose or other appropriate sugar compound. Specifically, the composition may have a glucose concentration of from about 2% to about 8%. Preferably, the glucose concentration may be about 4%.

The electrolytes of the composition can be selected, for example, from the group consisting of sodium, potassium, phosphate, bicarbonate, sulfate, chloride, calcium, and magnesium. For example, the fluid may contain from about 1 meq/l to about 5 meq/l potassium and from about 15 meq/l to about 30 meq/l sodium. Preferably, the composition may contain about 2 meq/l potassium and about 26 meq/l sodium. Also, the composition may contain phosphate in concentrations varying from about 2 meq/l to about 8 meq/l. Specifically, the phosphate concentration may be about 4 meq/l.

The novel fluid may also contain citric acid, citrate, preservatives, flavorings, artificial sweeteners, vitamins, minerals, and other compounds appropriate in a beverage of this type. The novel fluid may also be carbonated.

EXAMPLE 2

In order to provide a readily available source of energy for cells, the composition of the subject invention can contain pyruvate, lactate, or a combination of the two. It has been found that sufficient concentrations of pyruvate are necessary for the proper entrance of carbohydrates and fats into the Krebs cycle. During the course of strenuous exercise, the concentration of pyruvate available to cells can decrease markedly. By ingesting pyruvate, it is possible to maintain sufficient plasma concentrations so that the cells are able to utilize pyruvate as an energy source and so that fats can be effectively metabolized. According to the subject invention, lactate may be used instead of, or in addition to, pyruvate.

The concentration of pyruvate, lactate, or the combination of the two, may be from about 0.5% to about 10%. Preferably, the concentration of pyruvate, lactate, or a combination of the two is between about 1% and about 1.5%. When glycerol at about 1% and pyruvate at about 1% are both added to an appropriate glucose-electrolyte solution so that the osmotic pressure of the solution does not exceed 400 milliosmol, performance and endurance are enhanced. The level of enhancement achieved by the composition containing glucose, electrolytes, glycerol, and pyruvate is beyond the effect of the glucose-electrolyte solution alone, the glucose-electrolyte solution plus glycerol, or the glucose-electrolyte solution plus pyruvate. Best performance is achieved if the solution is kept between 300 and 350 milliosmol.

EXAMPLE 3

The composition of the subject invention may be designed for intravenous use. Intravenous use may have application in humans and in other animals. In the case of humans, intravenous use may be necessary when, for example, a person has fainted or otherwise become unconscious as a result of, for example, over-exertion and/or overexposure to sunlight, heat, or hemorrhage and loss of blood.

For intravenous application, no flavoring compounds would be present. Also, a neutral pH would be needed, therefore, no acidic compounds would be present in concentrations sufficient to significantly alter the pH of the saline solution.

The composition of the subject invention can also be used as a temporary substitute for blood. For example, in trauma cases where there has been a large loss of blood, this fluid can be given to replenish the blood volume. Also, during heart surgery or other surgical procedures where a heart-lung machine is used, the novel composition can be used to prime the heart-lung machine, thereby helping the patient to maintain plasma volume and to provide energy to help ameliorate the physiological trauma of surgery. Also, by maintaining vascular volume, complications such as post-surgical acute renal failure can be minimized.

For use as a blood substitute, the composition will comprise, preferably, water, electrolytes, glucose, and glycerol. Sucrose and citric acid are to be avoided when the composition is given intravenously. When used as a blood substitute, the composition of the subject invention may also comprise pyruvate and/or lactate.

An experiment has been conducted on rats to assess the effects of the administration of $TQ_2$ after blood loss. A total of nine male rats were used in this experiment. They varied in body weight from 280 to 350 g. Prior to the experiment, all rats were maintained in a temperature controlled room at 25°±2° C., which was illuminated from 7:00 am to 7:00 pm. The mean blood pressure of the rats prior to the experiment was in the range of around 90 mm Hg to 120 mm Hg. All animals were allowed tap water and food (Purina Laboratory Chow #5001) ad libitum.

All rats had arterial and venous cannula placed in the right femoral artery and vein, respectively, two weeks prior to the experiment. When the experiment began, each unanesthetized rat was placed alone in a stainless steel cage, and the arterial cannula was coupled to a pressure transducer which was coupled to a previously calibrated NarcoBio Instruments Company polygraph. After a control period of 30 minutes, during which mean blood pressure was recorded for each rat, blood was removed slowly during a 30 minute period until mean blood pressure was 60 mm Hg. Blood pressure was maintained at this level for 20 minutes, after which 3 rats received warm (37° C.) isotonic NaCl solution intravenously at a volume equivalent to the amount of blood removed. An additional 4 rats received warm $TQ_2$ at a volume equivalent to the amount of blood removed. The $TQ_2$ composition used in this experiment consisted of water, electrolytes, 3% glucose, about 2% glycerol, and about 2% pyruvate. The pH of the solution was about 7.0, and the osmotic pressure was about 290 milliosmol. A pH of approximately 7.0 can be maintained by use of an appropriate buffer system such as $NaH_2PO_4:Na_2HPO_4$ in a ratio of 1:4. One additional rat received nothing after its mean blood pressure had been reduced to 60 mm Hg for 20 minutes.

The results of this study are shown in Table 1. Of the three rats that received saline, mean blood pressure had increased 10 mm Hg 30 minutes later. Of the four rats that received $TQ_2$, mean blood pressure also increased 10 mm Hg 30 minutes later. The striking difference occurred in survival 24 hours later. Of the 3 saline-treated rats, only 1 survived; of the $TQ_2$-treated rats, 3 survived. The rat that received nothing did not survive for 24 hours. Thus, there was enhanced survival in rats treated with $TQ_2$ compared with those treated with saline, demonstrating the efficacious effect of $TQ_2$.

TABLE 1

Effect of hemorrhage on survival of rats receiving either saline, $TQ_2$, or nothing.

| Group | Number of Rats | Change in Mean Blood Pressure at 30 min. (mm Hg) | Number Surviving at 24 hours | (%) |
|---|---|---|---|---|
| Saline | 3 | +10 | 1 | (33) |
| $TQ_2$ | 4 | +10 | 3 | (75) |
| Nothing | 1 | +1 | 0 | (0) |

EXAMPLE 4

A fluid composition similar to that described in Example 1 may be administered to animals which are subject to strenuous exercise such as races and agricultural work. The exact composition of the fluid as well as the concentrations of its components may depend upon what type of animal is receiving the treatment. The teachings of this document combined with the expertise of one skilled in the biological and medical sciences would enable the practitioner to adjust the composition of the fluid in order to accommodate the needs of a particular animal.

The administration of the novel fluid could be orally, intravenously, or by other means capable of delivering the fluid to the tissues of the recipient animal. If the fluid is to be delivered orally, such a composition could contain flavoring which would make the fluid attractive to the animal. For example, for horses, the fluid could be flavored with an oat extract.

EXAMPLE 5

To enhance the beneficial effects of the novel fluid composition described here, caffeine may be added. The concentration of caffeine may range from about 50 mg/l to about 5000 mg/l.

EXAMPLE 6

The novel fluid composition described here may also be used to help maintain the weight and health of agricultural animals subjected to heat stress. Heat stress may occur, for example, on the open range, in zoos, and during the transportation of animals.

The fluid may be administered in any of the ways previously described. If administered orally, the fluid may be combined with appropriate flavorings to make it attractive to the animals.

EXAMPLE 7

The novel fluid composition described here may also be used to alleviate the effects of volume depletion which is a problem which has been observed in astronauts.

EXAMPLE 8

The use of glycerol in a beverage could also be used in areas of cold environment where it would reduce tissue damage due to frostbite and extreme cold. Such a glycerol beverage would allow distribution of the glycerol into the tissues, particularly in the extremities, fingers and toes, which are affected most by crystallization in the tissues and by diminished blood flow. Glycerol has been found to be distributed throughout the body in ten minutes after ingestion; thus, it could be used to rapidly provide protection from extreme cold. This could be especially useful, for example, for football players who must play in cold climates, but who cannot or do not wish to wear gloves or other protective covering.

Also, it is well established that dehydration can be a serious problem which accompanies prolonged exposure to cold temperatures. Because the subject composition can be utilized to achieve proper water allocation and prevent blood plasma volume depletion, it can be used to ameliorate the effects of dehydration caused by exposure to cold temperatures. Thus, the novel composition can be used advantageously by skiers or by army personnel in cold climates.

EXAMPLE 9

The optimal rate of administration of the novel composition described here can depend upon the physiological characteristics of the individual receiving the fluid, the nature of the physical exertion or exposure, and the environmental conditions. However, a standard rate of application would be approximately 170 to 260 ml of fluid every 15 to 20 minutes, starting approximately 15 minutes before the exercise or exposure is commenced. If significant sweating is occurring, as would be expected in hot environments or with physical exertion, the intake of fluid should be adjusted so that the volume ingested approximates the amount of fluid lost through sweating. When the fluid is ingested to alleviate the dehydration accompanying prolonged exposure to cold temperature, the quantity of fluid ingested may be less than that which is necessary to achieve the desired effects in hot climates.

The ratio of ingredients in the composition may also be adjusted for changing environmental or physiological conditions. For example, in cold weather, the composition may contain a greater concentration of glycerol and a reduced concentration of electrolytes. Also, for individuals who desire a lower calorie drink, the sugar may be replaced with an artificial sweetener such as aspartame. For individuals who are concerned about high blood pressure, the drink can contain reduced concentrations of sodium.

EXAMPLE 10

The composition of the subject invention may also be prepared in a dehydrated, powder, or concentrate form for convenience of sale or shipment. When formulated in this way, the product could be reconstituted by the addition of water. The preparation of such a product in the dehydrated, powder, or concentrate form is well known to those skilled in the art. See for example, U.S. Pat. Nos. 4,042,684 and 4,322,407. Although glycerol cannot be provided in powder form, it can be provided separately or in a mixture of the other ingredients in a reduced water volume to facilitate bulk shipping.

We claim:
1. A fluid composition comprising:
   (a) water;
   (b) electrolytes;
   (c) at least one sugar compound selected from the group consisting of glucose, fructose, and sucrose;
   (d) glycerol in a concentration of from about 0.5% to about 5.0%; and
   (e) lactate.
2. The fluid composition, according to claim 1, wherein the concentration of lactate is between about 0.5% and about 10%.
3. The fluid composition, according to claim 2, further comprising pyruvate, wherein the total concentration of pyruvate and lactate is between about 0.5% and about 10%.
4. The fluid composition, according to claim 3, comprising the following ingredients:

| Ingredient | Approximate Concentration |
| --- | --- |
| Potassium | 2 meq/L |
| Sodium | 26 meq/L |
| Glucose | 4% |
| Glycerol | 1% |
| Pyruvate | 0.5% |
| Lactate | 0.5% |

-continued

| Ingredient | Approximate Concentration |
|---|---|
| Caffeine | 150 mg/L |
| Water | balance. |

5. A dehydrated, powder, or concentrate composition which, when reconstituted with water, forms a composition comprising water, electrolytes, glycerol, and at least one compound from the group consisting of pyruvate and lactate, wherein the combined concentration of said pyruvate and lactate is between about 0.5% and about 10%.

* * * * *

UNITED STATES PATENT AND TRADEMARK OFFICE
CERTIFICATE OF CORRECTION

PATENT NO. : 5,147,650

DATED : September 15, 1992

INVENTOR(S) : Melvin J. Fregly, R. Malcolm Privette, Robert Cade

It is certified that error appears in the above-identified patent and that said Letters Patent is hereby corrected as shown below:

Column 5: line 25: "oxygen on" should read --oxygen uptake on--.
Column 8: line 21: "trail" should read --trial--.
Column 10: line 52: "the TQ$_2$-treated" should read --the 4 TQ$_2$-treated--.

Signed and Sealed this

Seventh Day of September, 1993

Attest:

BRUCE LEHMAN

*Attesting Officer*    *Commissioner of Patents and Trademarks*